United States Patent [19]
Boussignac et al.

[11] Patent Number: 5,000,734
[45] Date of Patent: Mar. 19, 1991

[54] PROBE INTENDED TO BE INTRODUCED WITHIN A LIVING BODY

[76] Inventors: Georges Boussignac, 1 Allée de Provence, 92160 Antony; Jean-Claude Labrune, 19a rue Massenet, Sevres, both of France

[21] Appl. No.: 392,966
[22] PCT Filed: Jan. 26, 1989
[86] PCT No.: PCT/FR89/00025
  § 371 Date: Aug. 4, 1989
  § 102(e) Date: Aug. 4, 1989
[87] PCT Pub. No.: WO89/06983
  PCT Pub. Date: Aug. 10, 1989

[30] Foreign Application Priority Data
  Feb. 1, 1988 [FR] France .............. 88 01120

[51] Int. Cl.$^5$ ............................. A61M 25/10
[52] U.S. Cl. ........................... 604/96; 606/194
[58] Field of Search ................ 606/191, 194; 604/49–55, 96–103, 280, 283; 128/207.15

[56] References Cited

U.S. PATENT DOCUMENTS

| | | | |
|---|---|---|---|
| 4,183,102 | 1/1980 | Guiset | 604/101 |
| 4,289,128 | 9/1981 | Rüsch | 128/207.15 |
| 4,299,237 | 11/1981 | Foti. | |
| 4,423,725 | 1/1984 | Baran et al. | |
| 4,581,017 | 4/1986 | Sahota. | |
| 4,762,129 | 8/1988 | Bonzel | 604/96 |

FOREIGN PATENT DOCUMENTS

8401513 4/1984 World Int. Prop. O. .
8800071 1/1988 World Int. Prop. O. .

*Primary Examiner*—C. Fred Rosenbaum
*Assistant Examiner*—William W. Lewis
*Attorney, Agent, or Firm*—Fisher, Christen & Sabol

[57] ABSTRACT

A probe intended to be introduced within a living body, of the type comprising an elongated structure adapted to be introduced in a canal in said living body conveying a fluid, and presenting, at its end intended to be introduced in the canal, a single bag element connected to said structure, surrounding the latter and radially deformable so as to be able to come into contact with the inner wall of said canal. According to the invention, this probe is characterized in that it comprises at least one conduit (8), connected to said structure (3), extending at least substantially parallel to said structure (3) and outside the latter, over a distance corresponding substantially to the longitudinal dimension of said bag element (5), so as to be able to place in communication those parts (2a, 2b) of said canal (2) immediately upstream and downstream of said bag element (5) in order thus to maintain a minimum circulation of fluid in said canal (2).

13 Claims, 2 Drawing Sheets

PROBE INTENDED TO BE INTRODUCED WITHIN A LIVING BODY

The present invention relates to a probe intended to be introduced within a living body, of the type comprising an elorgoled structure adapted to be introduced into a canal in said living body conveying a fluid, and presenting, at its end intended to be introduced into the canal, a single bag element, connected to said structure, surrounding the latter and radially deformable so as to be able to come into contact with the inner wall of said canal.

Such "balloon" probes or so-called "expanding" catheters allow an intervention within a body canel, particularly a blood vessel, to treat disorders observed therein. Such disorders are generally constituted by deposite, atheromas, on the walls of the canal, bringing about stenoses thereof.

More particularly, such probes make it possible, on the one hand thanks to the radially deformable bag element, to improve the section of passage of the canal and, on the other hand, by injection of treatment product, for example through the walls of said bag element, to render long-lasting such re-establishment of the section of passage of the canal, possibly forming "in situ" a prosthesis of corresponding section.

However, during the intervention, it is necessary to maintain a minimum circulation of fluid in the body canal in order not to risk damaging the tissues or organs located downstream of the bag element, if the canal is blocked by the probe. Up to the present time, such fluid circulation is ensured either by perfusion of fluid brought from outside the body via a conduit provided in said elongated structure of the probe, or, as shown in U.S. Pat. No. 4 581 017, by "internal perfusion", lateral orifices open out in the canal being provided in said structure upstream and downstream of said bag element and being connected to one another by a "by-pass" traversing said strcture.

The first solution is not entirely satisfactory as it requires the supply of a fluid "outside" the body. Furthermore, in the two cases indicated herein-above, at least a part of the section, necessarily small, of the elogeted structure is used for the passage of the fluid, which, of course, renders more difficult, if not impossible, the passage in said structure of means for guiding the probe, or possibly of endo-scopic or surgical instruments, or the positioning of the means ensuring deformation of said bag element.

The present invention has for its object to avoid these drawbacks and relates to a probe, of the type indicated hereinabove, making it possible to maintain a minimum circulation of fluid in the body canal, whilst conserving a maximum section of free passage for said elogeted structure.

To that end, the probe, of the type indicated hereinabove, is noteworthy, according to the invention, in that it comprises at least one conduit, connected to said structure, extending at least substantially parallel to said structure and outside the latter, over a distance corresponding substantially to the longitudinal dimension of said bag element, so as to be able to place in communication those parts of said canal immediately upstream and downstream of said bag element, in order thus to maintain a minimum circulation of fluid in said canal.

In this way, the section of the said elogeted structure, at least at the level of said bag element, may be used to a maximum for the passage, as indiated herein-above, of means for guiding the probe, of endoscopic or surgical instruments, etc.

Each conduit may be made to pass on the periphery of said long structure, or on the periphery of said deformable bag element. However, it is advantageous if each conduit traverses said bag element.

Furthermore, said bag element being inflatable, according to another characteristic of the invention, each conduit is closed in the deflated state of said bag element and is open in the inflated state thereof.

According to another characteristic of the invention, the probe comprises a plurality of said conduits extending at least parallel with respect to one another.

Said conduits are advantageously angularly equi-distributed about the longitudinal axis of said structure.

In particular, the axes of said conduits extend over a cylindrical surface of which the longitidinal axis merges with that of said structure.

The Figures of the accompanying drawings will clearly show how the invention may be carried out. In these Figures identical refereces designate like elements.

Figure 1:
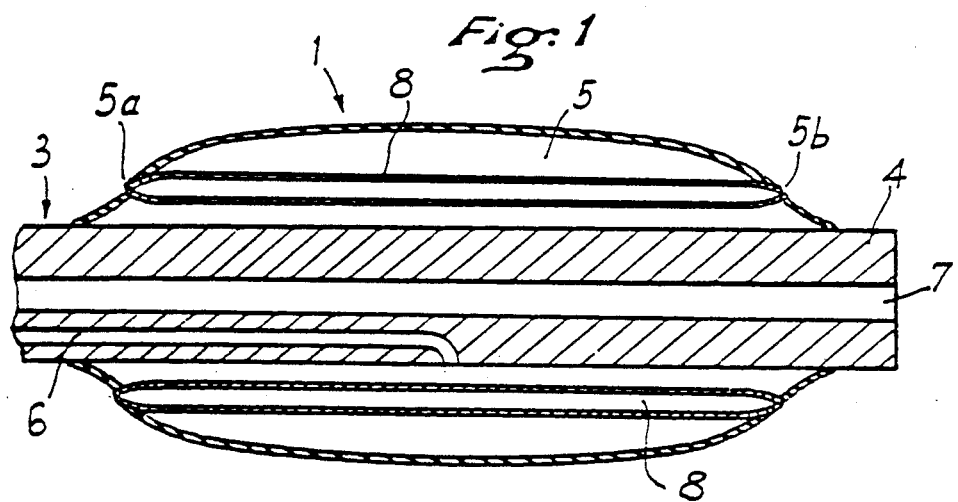
FIG. 1 is a schematic view in longitudinal section of the probe according to the invention, of which the deformable bag element is in the deflated state.

The probe 1, intended to be introduced in a body canal 2, for example a blood vassel, such as an artery, comprises an elogeted structure 3 of which only the end 4 intended to be introduced in the canal 2 is shown is the drawing, said end 4 presenting a bag element 5, connected to the structure 3, radially deformable, in particular inflatable by presssure means (not shown) connected to the bag element 5 by a tube 6 extending in the structure 3. In the inflated state, the bag element 5 comes into contact with the inner wall of the canal 2, as shown in FIG. 2, possibly re-estalishing the normal section of the canal.

Moreover, the structure 5 presents a slot 7 for the passage, for example, of guide means (not shown).

Figure 2:
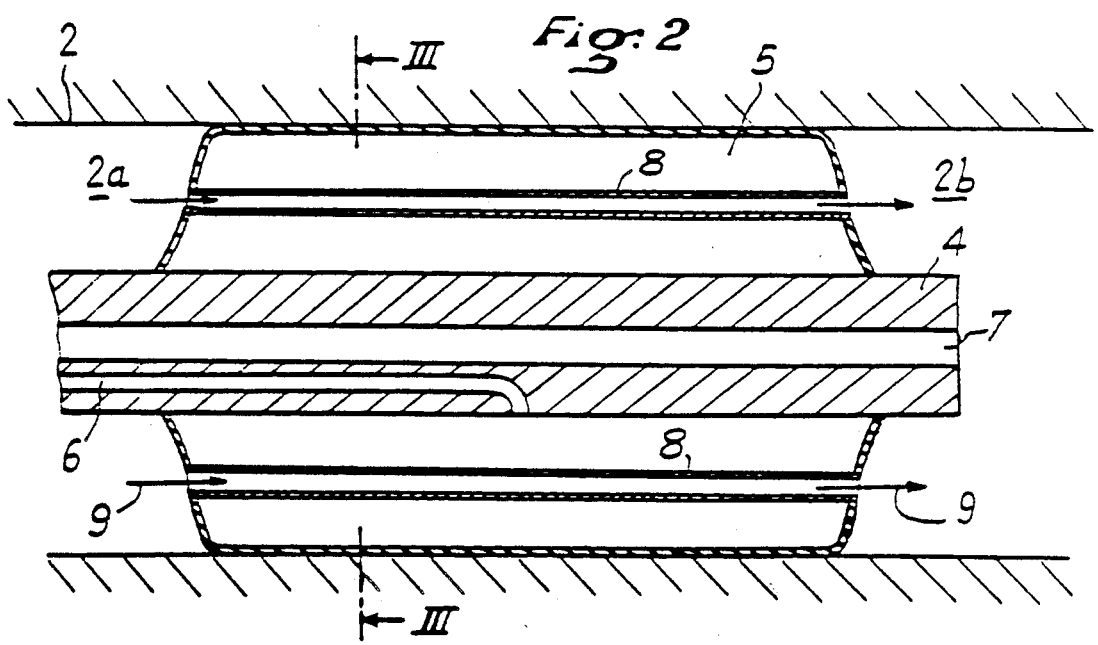
FIG. 2 is a schematic view similar to FIG. 1, the deformable bag element being in the inflated state.

According to the invention, a pluratlity of conduits 8 (four in the example shown in FIG. 3) pass through the bag element 5, extending at least substantially parallel to the structure 3, in order to place in communication part 2a of the canal 2 immediately upstream of the bag element 5 and part 2b of the canal 2 immediately downstream of said bag element, thus ensuring minimum circulation of fluid (arrows 9) during the intervention (FIG. 2).

Figure 3:
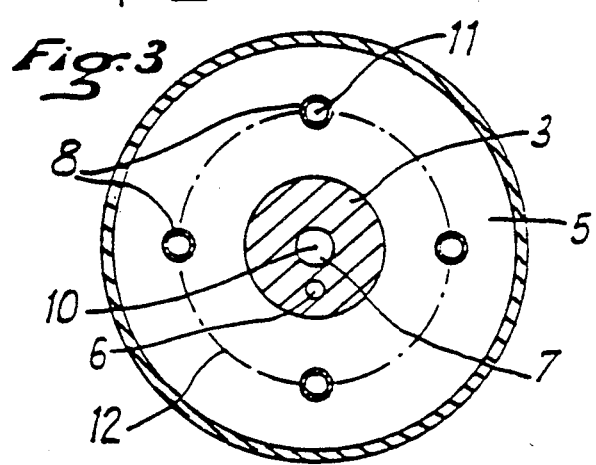
FIG. 3 is a view in transverse section along line III—III of FIG. 2.

As shown in FIG. 3, the conduits 8 are advantageously angularly equi-distributed about the longitudinal dinal axis 10 of the structure, in order thus to ensure a better distribution of the fluid in the downstream zone 2b of the canal 2. In particular, axes 11 of conduits 8 extend over a cylindrical surface (line 12 in FIG. 3) of which the longitudinal axis merges with the axis 10 of the structure 3.

Furthermore, conduits 8, open in the inflated state of the bag element 5 (FIG. 2), may be closed at least partially in the deflated state thereof (FIG. 1) due to the "collapse" of the ends 5a, 5b of the bag element 5 (FIG. 1).

The central conduit 7 may receive a guide allowing implantation in the injured part, an optical fiber allowing the injured part to be viewed or an optical fiber for a laser shot, the wave emitter being connected to the other end of the probe. The distal end of the probe at the level of the bag element 5 may comprise means, opaque to X-rays, for locating the displacment of the operational end of the probe and its correct positioning. The proximal end of the probe may be connected to a device for recirulation of the biological fluid under pressure, such as blood, intended for irrigating the organs served by the vessel in the course of treatment. In that case, the probe will be provided at its distal end with a pressure reducing valve which will prevent the risks of injury by the pressurized fluid. This pressure reducing valve will take up the principle of a decompression chamber and will generally be constituted by a supple sheath of latex for example, integrated at the end of the probe. It will eliminate the risks of traumatism provoked by the pressure of the recirculating biological fluid leaving the probe and is desirable in this type of probe, when it is installed and positioned in vessels serving organs sensitive to hypoxia (coronary arteries and brain).

Structure 3 may be made of plastics material, such as polyvinyl chloride, a polytetrafluoroethylene, a polyethylene. It may, partly or completely, be constituted by a steel wire helically wound with contiguous turns and be externally or internally coated with polytetrafluoroethylene. Conduits 8 may also be made of plastics material. The bag element 5 will generally be made of supple plastics material, elastically deformable to allow its volume to be increased. It will be pre-shaped to the desired dimension and/or shape.

Structure 3 may be manufactured by the conventional processes of extrusion. The same may apply for the conduits 8 whilst the bag element 5 will generally be obtained by mounlding. The conduits 8 and the bag element 5 may also be manufactured in one piece by moulding or by a process of manufacture of the same nature, this process of manufacture being desirable for reasons of safety. The uptakes of the exposure to rays may also be used to obtain the desired strengths and deformabilities.

Figure 4:
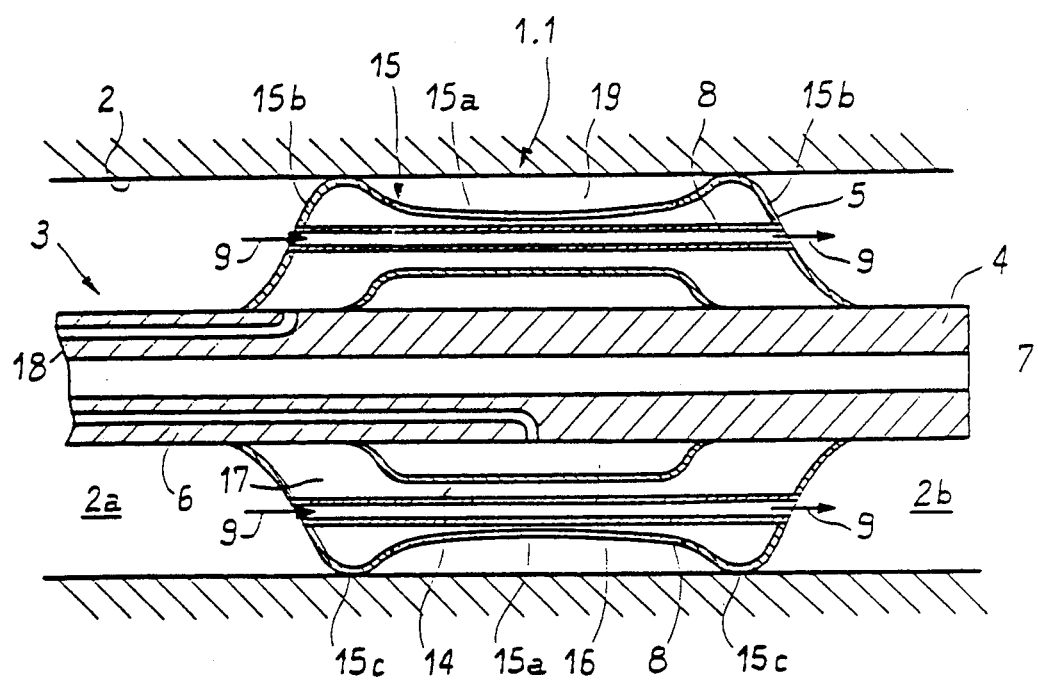
FIG. 4 illustrates a variant embodiment of the probe according to the invention, in the inflated state.

The variant 1.1 of the probe according to the present invention, shown in the inflated state within a body canal 2 in FIG. 4, comprises the elements 3 to 8 described hereinabove. In the probe 1.1, the bag element 5 comprises two walls 14 and 15. Inner wall 14 is enveloped by the outer wall 15 and defines with structure 3 an expansible chamber 16 in which tube 6 opens out. The outer wall 15, enveloping the inner wall 14, defines with the latter a chamber 17, possibly connected to the outside by a canal 18. The conduits 8 pass through said chamber 17. The outer wall 15 may comprise a porous central part 15a when the chamber 16 is under pressure. The ends 15b of the wall 15 may be pro-shaped to present, each, a peripheral bead 15c, said peripheral beads 15c surrounding the porous central part 15a.

In this way, the bag element 5 presents a double wall 14, 15 and its outer wall 15 comprises a portion 15a permeable under pressure, capable of allowing passage to the outside (i.e. in the space 19 defined between the canal 2, the beads 15c and the wall portion 15a) of a product capable of allowing a local treatment of said canal, for example a cytotoxic or cytostatic product, or an endoprosthesis. Such a fluid may be contained in the chamber 17 during introduction of the probe in the canal 2, or may be supplied thereto in the course of operation via conduit 18. It will be noted that the end beads 15c ensure a certain tightness with respect to space 19.

We claim:

1. Probe intended to be introduced within a living body, comprising:
   (a) an elongated tubueor structure adapted to be introduced in a canal in said living body conveying a fluid said elongated structure have a longitudinal axis;
   (b) a single bag element connected to said structure at the end of said elongated structure to be introduced into said canal, said bag element surrounding said elongated structure and being radially deformable so as to be able to come into contact with the inner wall of said canal, wherein said bag element comprises a plurality of conduits, said conduits being at least substantially parallel with respect to one and another, and said conduits being connected to said big element, said conduits extending at least substantially parallel to and outside of said elongated structure over a distance corresponding substantially to the length of said bag element, so as to be able to place in communication those parts of said canal immediately upstream and downstream of said bag element, in order to maintain a minimum circulation of fluid in said canal.

2. Probe according to claim 1, characterized in that said conduits are angularly equi-distributed about the logitudinal axis of said elongated structure.

3. Probe according to claim 2, wherein said conduits are equi-distant from the longitudinal axis of said elongated structure.

4. Probe according to claim 1 characterized in that said bag element includes a double wall 14, 15, comprising ann inner and an outer wall and an intersticial space disposed therebetween, and wherein said conduits pass inside this double wall, characterized in that the outer wall 15 of said double wall 14, 15 is at least partially porous under pressure, and wherein the inner wall 14 of said double wall 14, 15 forms an inflatable balloon.

5. Probe according to claim 4, wherein along the length of the outer wall of said bag element the cantral part 15a of said outer wall 15 is porous under pressure, and wherein the ends of said outer wall of said bag element are in the the form of raised beads 15c for more tightly contacting the inside walls of said canal.

6. Probe according to claim 5, further including a conduit 18 for supplying the intersticial space within said double wall 14, 15 with a substance capable of traversing said central part 15a of said outer wall 15 of said bag element.

7. Probe intended to be introduced within a living body, comprising:
   (a) an elongated tubulor structure, said elongated structure having a longitudinal axis and being adapted to be introduced in a canal in said living body conveying a fluid;
   (b) a single bag element connected to said structure at the end of said elongated structure to be introduced into said canal, said bag element surrounding said elongated structure and being radially deformable so as to be able to come into contact with the inner wall of said canal, wherein said bag element comprises at least one conduit connected to said big element, said at least one conduit extending at least substantially parallel to and outside of said elongated structure over a distance corresponding substantially to the length of said bag element, as to be able to place in communication those parts of said canal immediated upstream and downstream of said bag element, in order to maintain a minimum circulation of fluid in said canal, wherein said probe includes a plurality of said conduits at least substantially parallel with respect to one another.

8. Probe according to claim 7, wherein said conduits are angularly equi-distributed about the longitudinal axis of said elongated structure.

9. Probe according to claim 8, wherein said conduits are equi-distant from the longitudinal axis of said elongated structure.

10. Probe according to claim 7, characterized in that said bag element includes a double wall, said double wall comprising an inner and an outer wall and an intersticial space disposed therebetween and wherein said at least one conduit passes inside this double wall.

11. Probe according to claim 10, wherein the outer wall of said double wall is at least partially porous under pressure, and wherein the inner wall of said double wall forms an inflatable balloon.

12. Probe according to claim 11, wherein along the length of the outer wall of said bag element the central part of said outer wall is porous under pressure, and wherein the ends of said outer wall of said bag element are in the form of raised beads for more tightly contacting the inside walls of said canal.

13. Probe according to claim 12, further including a conduit for supplying the intersticial space within said double wall with a substance capable of traversing said central part of said outer wall of said bag element.

* * * * *